United States Patent [19]

Miyamoto

[11] Patent Number: 4,893,929
[45] Date of Patent: Jan. 16, 1990

[54] PARTICLE ANALYZING APPARATUS

[75] Inventor: Moritoshi Miyamoto, Kawasaki, Japan

[73] Assignee: Canon Kabushiki Kaisha, Tokyo, Japan

[21] Appl. No.: 165,497

[22] Filed: Mar. 8, 1988

[30] Foreign Application Priority Data

Mar. 13, 1987 [JP] Japan .................................. 62-58301
Jun. 12, 1987 [JP] Japan .................................. 62-146656

[51] Int. Cl.⁴ ...................... G01N 15/02; G01N 21/53
[52] U.S. Cl. .................................. 356/336; 356/338; 356/343
[58] Field of Search ...................... 356/336, 338, 343

[56] References Cited

U.S. PATENT DOCUMENTS 4,037,964  7/1977  Wertheimer et al. ............... 356/336
4,037,965  7/1977  Weiss ................................. 356/336

Primary Examiner—Davis L. Willis
Assistant Examiner—Matthew W. Koren
Attorney, Agent, or Firm—Fitzpatrick, Cella, Harper & Scinto

[57] ABSTRACT

A particle analyzing apparatus is provided with applying means for applying a light beam to a particle to be examined, correcting means for multiplying the intensities of a plurality of components of scattered lights emitted from said particle to be examined which differ in scattering angle by a correction coefficient and adding them together, and operation means for calculating the particle diameter of said particle to be examined from the output value of said correcting means.

4 Claims, 7 Drawing Sheets

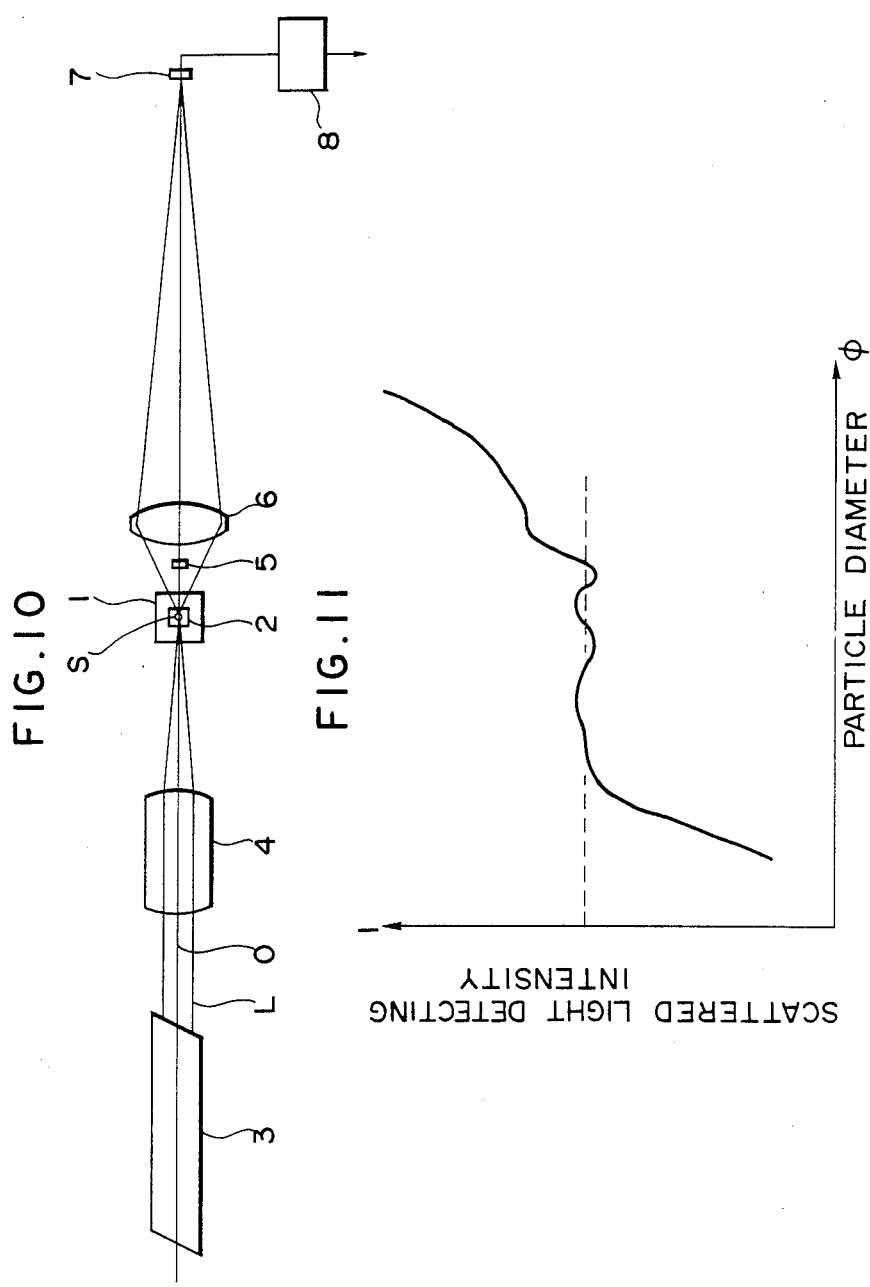

PARTICLE ANALYZING APPARATUS

BACKGROUND OF THE INVENTION

1. Field of the Invention

This invention relates to a particle analyzing apparatus for applying a light beam to a particle to be examined, photometering light emitted from the particle to be examined and analyzing the particle to be examined, and in particular to a particle analyzing apparatus for calculating the particle diameter of said particle to be examined from scattered lights emitted from said particle to be examined.

2. Related Background Art

In a conventional particle analyzing apparatus used in a flow cytometer or the like, an irradiating light is applied to sample liquid such as corpuscle cells wrapped in sheath liquid and passing through a circulating portion at the center of a flow cell which has, for example, a minute rectangular cross-section of 200 μm ×200 μm, and the resultant forward scattered light, sideways scattered light and fluorescent light are photometered to find the particulate properties such as the shape, size and refractive index of a particle to be examined, thereby accomplishing the analysis of the particle to be examined.

In FIG. 10 of the accompanying drawings, a particle S to be examined passes through a circulating portion 2 at the center of a flow cell which is perpendicular to the plane of the drawing sheet, and a laser source 3 is disposed in a direction orthogonal to this flow. On the optic axis 0 of the laser beam L emitted from this laser source 3, there is disposed an imaging lens 4 comprising two sets of cylindrical lenses orthogonal to each other disposed adjacent to the laser source 3 with respect to the particle S to be examined. Also, on the optic axis 0 on that side opposite to the laser source 3 with respect to the particle S to be examined, there are successively arranged a light-intercepting plate 5, a condensing lens 6 and a photoelectric detector 7. The output of the photoelectric detector 7 is connected to an operation circuit 8.

The laser beam L emitted from the laser source 3 is shaped into an imaging beam of any long or short diameter by the imaging lens 4 and is applied to the particle S to be examined flowing through the circulating portion 2. The laser light L which is not scattered by the particle S to be examined is prevented from rectilinearly travelling by the light-intercepting plate 5, and of the scattered lights scattered by the particle S to be examined, the forward scattered light is condensed on the photoelectric detector 7 through the condensing lens 6 and the properties of the particle S to be examined are measured. That is, generally, the forward scattered light detecting intensity corresponds to the particle diameter, and from this scattered light detecting intensity, the particle diameter can be calculated in the operation circuit 8.

However, in this example of the prior art, as shown in FIG. 11 of the accompanying drawings, the relation between the scattered light detecting intensity and the particle diameter is not a always increasing function, that is, the scattered light detecting intensity and the particle diameter is not in the relation of 1 to 1, when the particle to be examined is of a light-transmitting property, and this leads to the problem that measurement cannot be done in the vicinity of a certain particle diameter.

SUMMARY OF THE INVENTION

It is the object of the present invention to provide a particle analyzing apparatus which can accomplish accurate measurement of particle diameter irrespective of the particle to be examined.

BRIEF DESCRIPTION OF THE DRAWINGS

FIG. 10 shows the construction of an example of the prior art.

FIG. 11 is a graph showing the relation between the particle diameter and the scattered light intensity in the example of the prior art.

DESCRIPTION OF THE PREFERRED EMBODIMENTS

Figure 1:
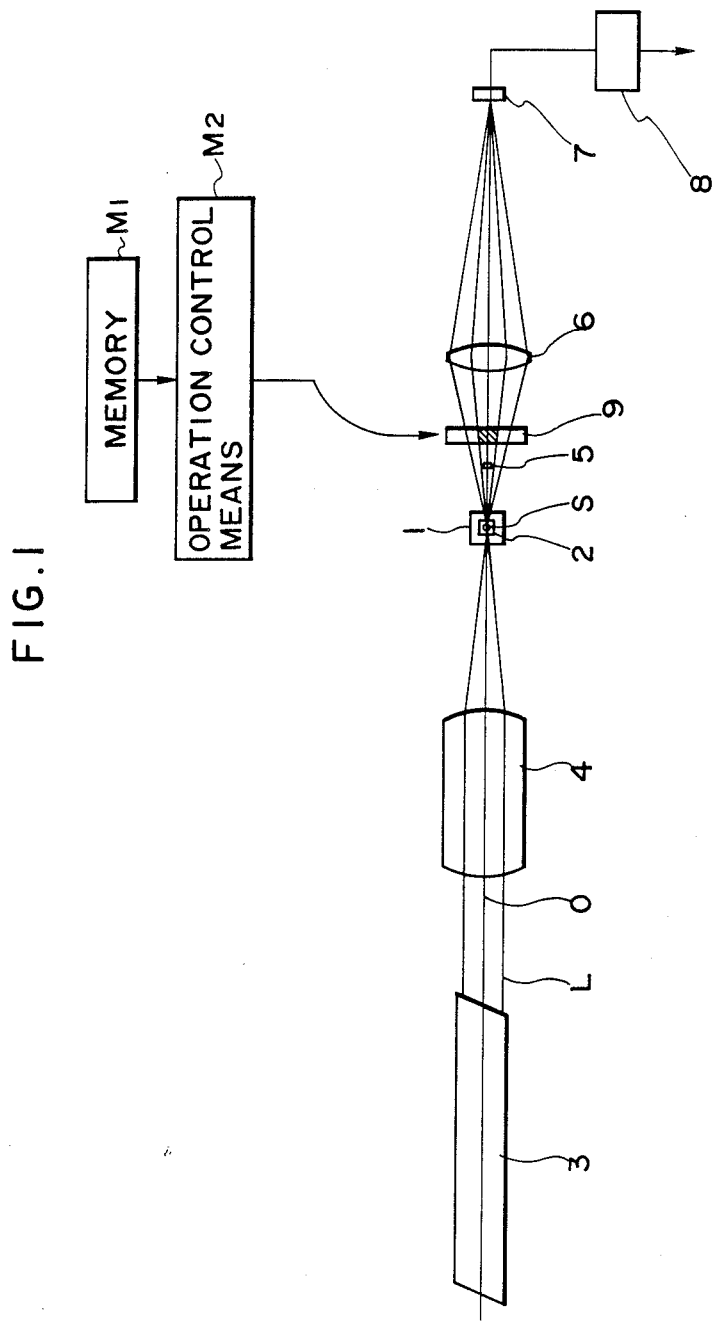
FIG. 1 shows the construction of a first embodiment of the present invention.

FIG. 1 shows a first embodiment of the present invention, and in FIG. 1, reference numerals similar to those in FIG. 10 designate similar members.

Figure 2:
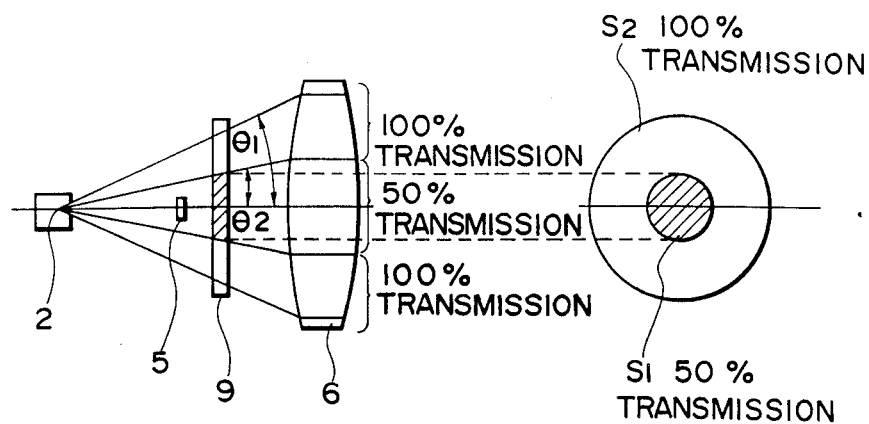
FIG. 2 is a detailed view of a filter.

In FIG. 1, the reference numeral 9 designates a filter disposed between a circulating portion 2 and a condensing lens 6 and having transmission factors of 50% and 100% in circumferential areas $S_1$ and $S_2$, respectively, corresponding to scattering angles $0-\theta_1$ and $\theta_1-\theta_2$, as shown in FIG. 2.

Figure 3:
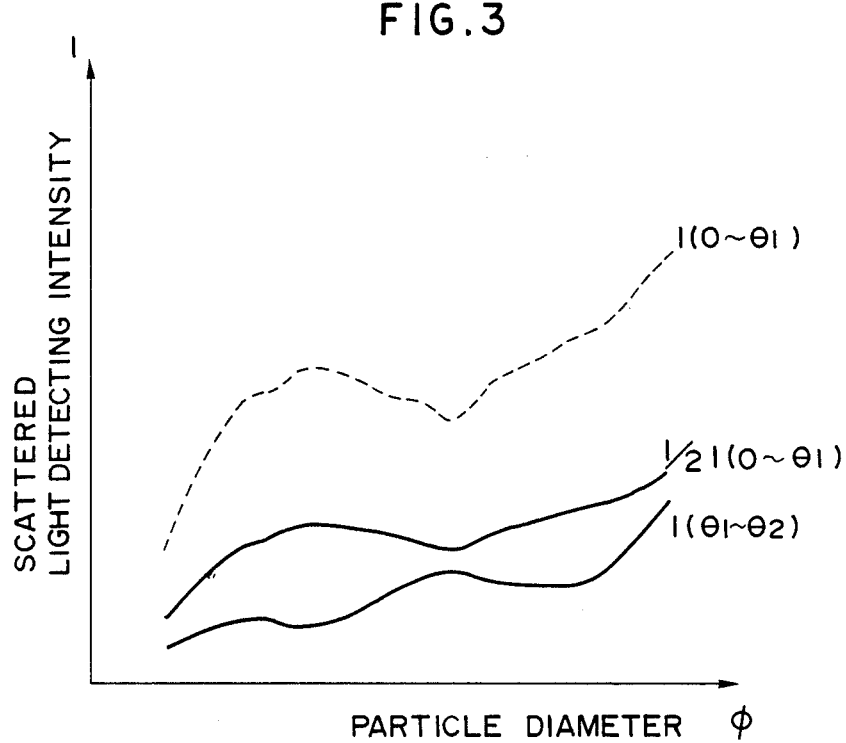
FIGS. 3 and 4 are graphs showing the relation between the particle diameter and the scattered light intensity according to the present invention.
Figure 4:
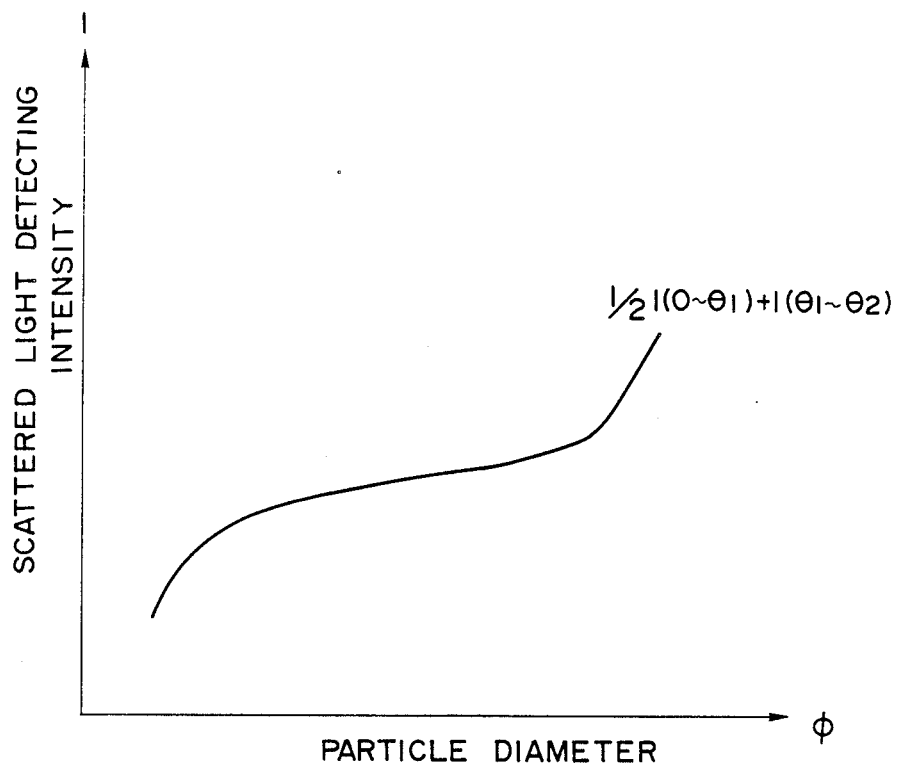

The applicant has found that the relation between the scattered light detecting intensity I and the particle diameter $\phi$ differs in conformity with the scattering angle $\theta$ as shown in FIG. 3, and on this premise, by the use of the filter 9, the scattered light detecting intensities $I(0-\theta_1)$ and $I(\theta_1-\theta_2)$ at the scattering angles $0-\theta_1$ and $\theta_1-\theta_2$ are not simply added as has been done in the past, but the scattered light detecting intensity $I(0-\theta_1)$ in the area of the scattering angle $0-\theta_1$ is multiplied by a coefficient and added to $I(\theta_1 - \theta_2)$. Thereby the scattered light detecting intensity I becomes a always increasing function of the particle diameter $\phi$, as shown in FIG. 4.

In FIG. 1, memory $M_1$ stores therein the scattered light detecting intensities $I(0-\theta_1)$ and $I(\theta_1-\theta_2)$ regarding the respective particle diameters $\phi$ at the scattering angles $0-\theta_1$ and $\theta_1-\theta_2$ shown in FIG. 3, and operation is effected by operation control means $M_2$ so that the aforementioned always increasing function is obtained, and for example, a turret is rotated to select a suitable filter 9 from among a plurality of filters and set it in the optical path.

Figure 5:
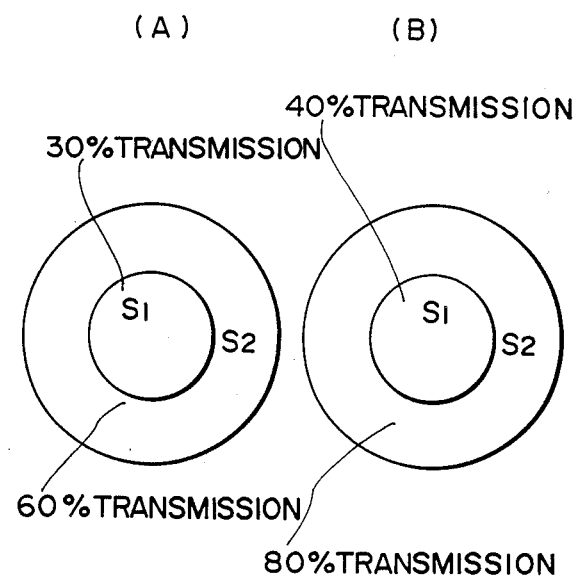
FIGS. 5 and 6 show modifications of the first embodiment.

In the above-described embodiment, the transmission factors of 50% and 100% have been provided for the areas $S_1$ and $S_2$ corresponding to the scattering angles $0-\theta_1$ and $\theta_1-\theta_2$, but as shown in FIGS. 5(A) and (B), a transmission factor ratio of 1 to 2 such as 30% and 60%, or 40% and 80%, or 20% and 40% may be provided for the areas $S_1$ and $S_2$ corresponding to the scattering angles $0-\theta_1$ and $\theta_1-\theta_2$, thereby obtaining a similar effect.

Figure 6:
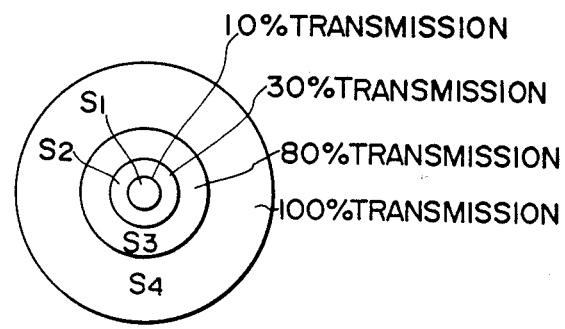

Also, in the above-described embodiment, use has been made of an optical filter divided into two layers $S_1$ and $S_2$, but alternatively, the filter may be divided into more layers (e.g. four layers $S_1$, $S_2$, $S_3$ and $S_4$) as shown in FIG. 6.

That is, generally assuming that the scattered light detecting intensities for the scattering angles $0-\theta_1$, $\theta_1-\theta_2$, $\theta_2-\theta_3$, . . . are $I(0-\theta_1)$, $I(\theta_1-\theta_2)$, $I(\theta_2-\theta_3)$, . . . , a transmission factor distribution is provided so that an always increasing function is obtained as $I = a_1 \cdot I(0-\theta_1) + a_2 \cdot I(\theta_1-\theta_2) + a_3 \cdot I(\theta_2-\theta_3) + \ldots$ ($a_i$ is a weight coefficient).

Although an optical filter has been used in the above-described embodiment, liquid crystal electrically variable in the transmission factor of each area may be used instead of the optical filter. In such case, the liquid crystal will be controlled by the operation control means $M_2$ so that the aforementioned always increasing function may be obtained.

The position of the filter is not limited to the position between the circulating portion 2 and the condensing lens 6, but the filter may be disposed between the condensing lens 6 and a photoelectric detector, or for example the surface of the condensing lens 6 may be provided with coating having a predetermined transmission factor distribution conforming to the scattering angle so that the condensing lens 6 itself may have a function similar to that of the filter.

Further, in the above-described embodiment, a light-intercepting plate 5 has been provided discretely from the light control means such as the filter 9, but alternatively, the light control means itself such as the filter 9 may have the light-intercepting characteristic of intercepting light in the area near the optic axis, or the light-intercepting plate 5 may be adhesively secured to the light control means such as the filter 9.

Figure 7:
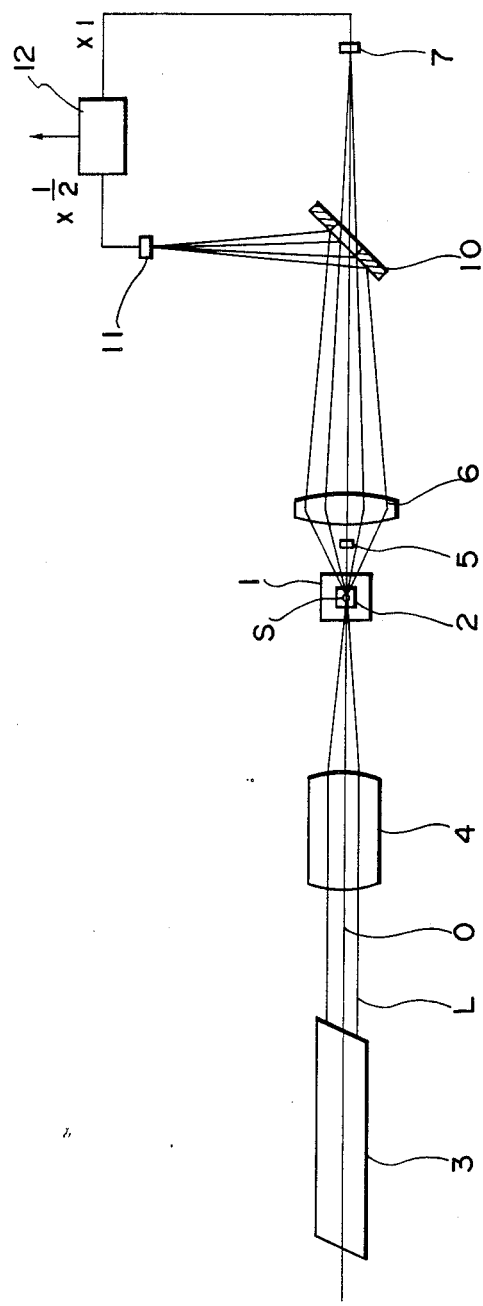
FIG. 7 shows the construction of a second embodiment of the present invention.

FIG. 7 shows a second embodiment of the present invention, and in FIG. 7, reference numerals similar to those in FIG. 10 designate similar members.

In FIG. 7, the reference numeral 10 designates an apertured mirror. A first photoelectric detector 7 is provided in the rectilinear direction of the apertured mirror 10, and a second photoelectric detector 11 is provided in the direction of reflection of the apertured mirror 10. The outputs of the first and second photoelectric detectors 7 and 11 are connected to an operation circuit 12.

Of the lights scattered by the particle S to be examined, the light from the vicinity of the angle O to the angle $\theta_1$ passes intactly through the apertured mirror 10 and is photometered by the first photoelectric detector 7, and the light from the angle $\theta_1$ to the angle $\theta_2$ is reflected by the apertured mirror 10 and is photometered by the second photoelectric detector 11.

As shown in FIG. 3, the relation between the scattered light detecting intensity I and the particle diameter $\phi$ differs in conformity with the scattering angle $\theta$, and the scattered light up to the scattering angle $0-\theta_1$ and the scattered light up to the scattering angle $\theta_1-\theta_2$ are discretely detected by the use of the apertured mirror 10, and for the respective scattered light detecting intensities $I(0-\theta_1)$ and $I(\theta_1-\theta_2)$, $I(0-\theta_1)$ is multiplied by a coefficient in the operation circuit 12 and added to $I(\theta_1-\theta_2)$ Thereby, the scattered light detecting intensity I becomes a always increasing function of the particle diameter $\phi$, as shown in FIG. 4.

Figure 8:
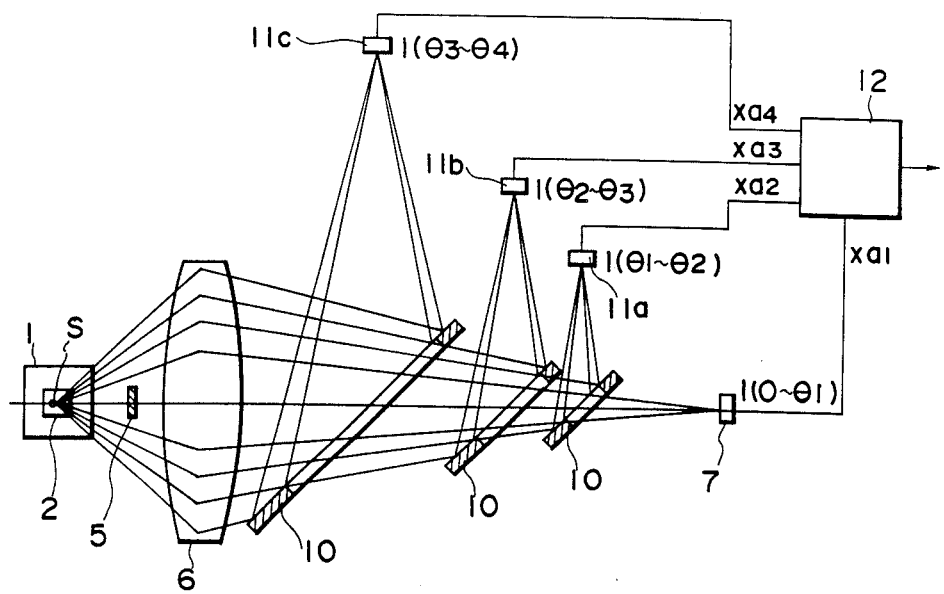
FIGS. 8 and 9 show modifications of the second embodiment.

In the above-described embodiment, a single apertured mirror 10 has been used and operation has been effected with the light divided into two scattering angle components, but alternatively, as shown in FIG. 8, a plurality of apertured mirror 10a, 10b and 10c and photoelectric detectors 7, 11a, 11b and 11c may be used and operation may be effected with the light divided into a plurality of scattering angle components. That is, generally assuming that the scattered light detecting intensities for the scattering angles $0-\theta_1$, $\theta_2-\theta_3$, $\theta_3-\theta_4$, . . . are $I(0-\theta_1)$, $I(\theta_2-\theta_3)$, $I(\theta_3-\theta_4)$, . . . , there is obtained a always increasing function which provides $I = a_1 \cdot I(0-\theta_1) + a_2 \cdot I(\theta_1-\theta_2) + a_3 \cdot I(\theta_2-\theta_3) +$ The correction coefficient $a_n$ is not limited to $0 < a_n \leq 1$, but may be set to any value so that the always increasing function may be obtained.

Figure 9:
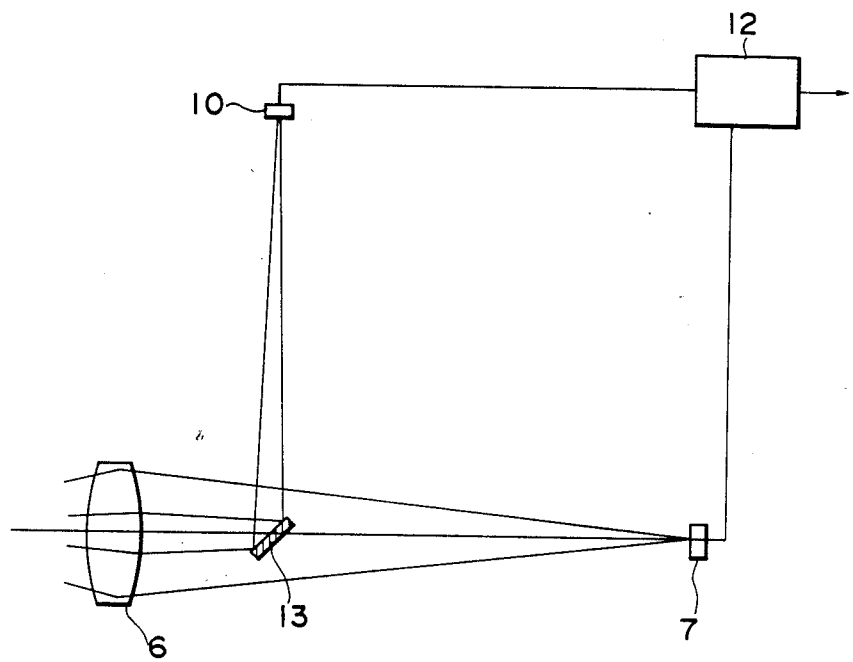

Also, in the above-described embodiment, the apertured mirror 10 is disposed between the condensing lens 6 and the photoelectric detector 7, but alternatively, the apertured mirror 10 may be disposed at any position in the photometering optical system, such as, for example, between the flow cell 1 and the condensing lens 6. Further, as shown in FIG. 9, an unapertured small mirror 13 may also be used to obtain a similar effect.

I claim:

1. A particle analyzing apparatus comprising:
   irradiating means for applying a light beam to a particle to be examined flowing through an observation portion;
   a plurality of light detecting means for respectively detecting intensities of a plurality of components of scattered light emitted from said particle to be examined at the same moment and which differ in scattering angle;
   correcting means for multiplying outputs of said plurality of light detecting means by correction coefficients and adding them together and providing an output value; and
   operation means for calculating the particle diameter of said particle to be examined from the output value of said correcting means;
   the output value of said correcting means and said particle diameter being in the relation of 1 to 1.

2. A particle analyzing apparatus according to claim 1, wherein said irradiating means has a laser beam source.

3. A particle analyzing apparatus comprising:
   irradiating means for applying a light beam to a particle to be examined flowing through an observation portion;
   a plurality of light detecting means for respectively detecting intensities of optically separated first and second scattered light emitted from said particle to be examined at the same moment;
   correcting means for multiplying outputs of said plurality of light detecting means by correction coefficients and adding them together and providing an output value; and
   operation means for calculating the particle diameter of said particle to be examined from the output value of said correcting means;
   the output value of said correcting means and said particle diameter being in the relation of 1 to 1.

4. A particle analyzing method comprising the steps of:
   irradiating a light beam to a particle to be examined flowing through an observation portion;
   detecting intensities of scattered light of optically separated first and second light fluxes emitted from said particle to be examined at the same moment respectively in the scattered light from said particles;

multiplying the detected intensities of the scattered light by correction coefficients and adding them together to provide an added value; and calculating the particle diameter of said particle to be examined from said added value;

said added value and said particle diameter being in the relation of 1 to 1.

* * * * *